United States Patent [19]

Tarbutton

[11] 4,186,251

[45] Jan. 29, 1980

[54] COMPOSITION AND METHOD FOR DETERMINATION OF CHOLESTEROL

[75] Inventor: Peter N. Tarbutton, Elkhart, Ind.

[73] Assignee: Miles Laboratories, Inc., Elkhart, Ind.

[21] Appl. No.: 337,189

[22] Filed: Mar. 1, 1973

[51] Int. Cl.² ............................................. G01N 31/14
[52] U.S. Cl. ...................................... 435/11; 435/190; 435/863; 435/872
[58] Field of Search .................... 195/103.5 R, 99, 127

[56] References Cited

U.S. PATENT DOCUMENTS

| | | | |
|---|---|---|---|
| 3,092,465 | 6/1963 | Adams et al. | 195/103.5 R |
| 3,099,605 | 7/1963 | Free | 195/103.5 R |
| 3,183,173 | 5/1965 | Oakes | 195/103.5 R |
| 3,607,093 | 9/1971 | Stone | 195/103.5 R |
| 3,776,816 | 12/1973 | Terada et al. | 195/103.5 R |

FOREIGN PATENT DOCUMENTS 2047147  12/1971  France ............................... 195/103.5 R

OTHER PUBLICATIONS

Clayton, Methods in Enzymology, vol. XV, pp. 528-529, (1969).

*Primary Examiner*—Alvin E. Tanenholtz
*Attorney, Agent, or Firm*—Andrew L. Klawitter

[57] ABSTRACT

The present invention relates to compositions and methods for use in determining free and total cholesterol levels in fluids such as body fluids. A test for free cholesterol is disclosed based on the determination of hydrogen peroxide released through the action of a chemical system having cholesterol oxidase activity on free cholesterol. A preferred means for determining the released hydrogen peroxide involves the use of a substance having peroxidative activity and an oxidation-reduction indicator. The addition of a chemical system having cholesterol ester hydrolase activity to the free cholesterol test composition provides an integral test composition for the determination of total cholesterol.

5 Claims, 1 Drawing Figure

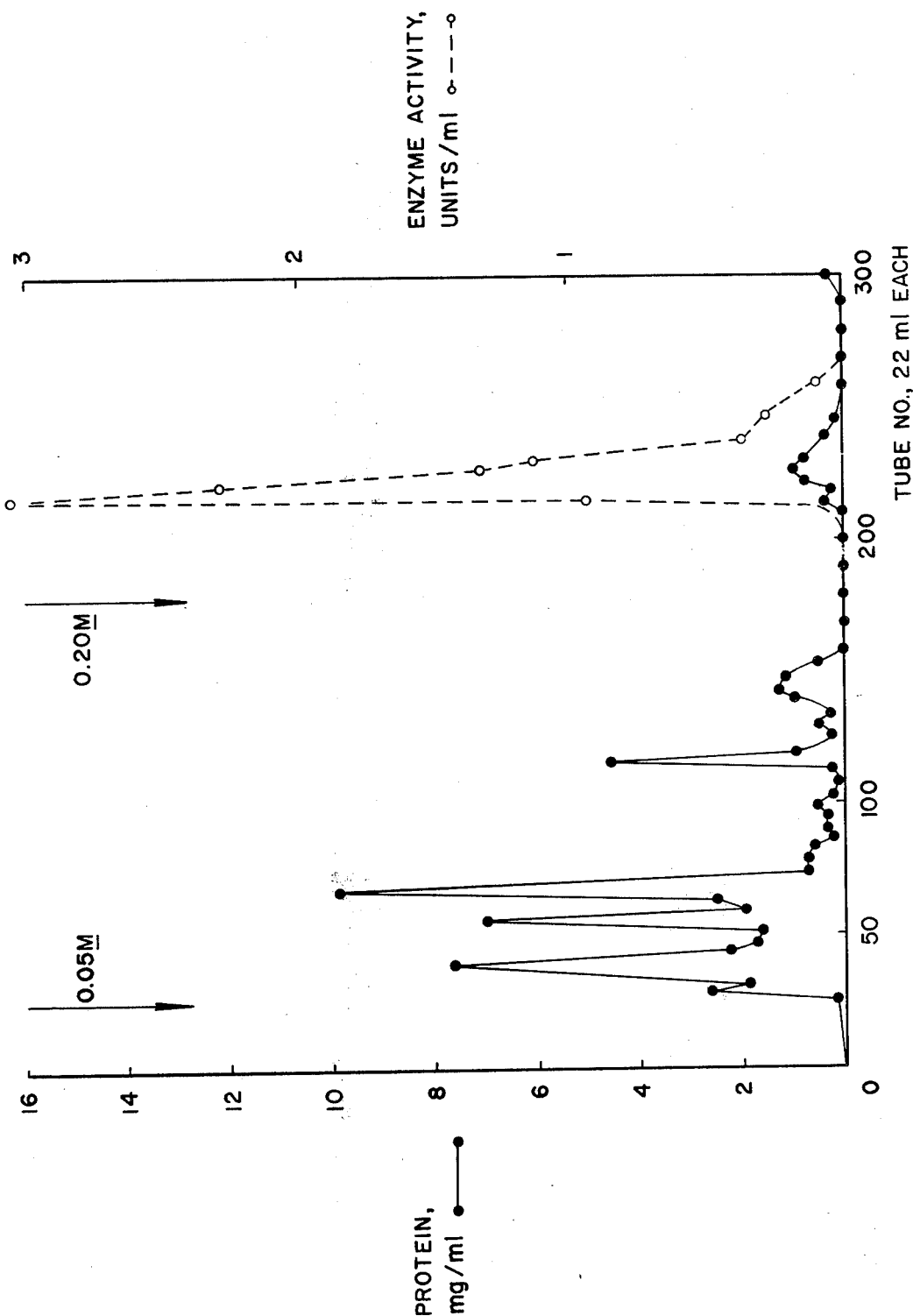

COMPOSITION AND METHOD FOR DETERMINATION OF CHOLESTEROL

BACKGROUND OF THE INVENTION

Cholesterol is found in nearly all plant and animal cells, either in its free form or in an ester form. Free cholesterol refers to cholesterol in its unreacted state ($\Delta^5$-cholesterol, or cholest-5-en-3$\beta$-ol). Total cholesterol refers to the sum of free cholesterol and its ester derivatives such as the linoleate, oleate, palmitate, arachidonate, palmitoleate, linolenate, stearate, and myristate esters. Cholesterol is found in constant amounts in serum under normal conditions. In general, 25% of the total cholesterol level in serum is free cholesterol while the remaining 75% is in the form of ester derivatives.

It is fairly well established that the total cholesterol content of whole blood is directly related to certain maladies in man and animals. Among the many maladies which have been found to be related to total cholesterol levels in blood are hepatocellular diseases, thyroid metabolism disorders, biliary obstruction and perhaps most importantly atherosclerosis and other vascular difficulties. Until the last decade it was customary to determine the total cholesterol content of whole blood, but it is now known that the serum level is altered by factors which do not affect the red cell level. As a result, most clinical determinations of both free and total cholesterol are performed on serum rather than on whole blood.

DESCRIPTION OF THE PRIOR ART

As the clinical significance of free and total cholesterol levels become increasingly accepted, the need for rapid and reliable methods for determining cholesterol in fluids resulted in research efforts which yielded numerous new procedures and modifications of basic conventional procedures. A general treatise of the vast methodology available in cholesterol determinations can be found in *American Journal of Clinical Pathology* Vol. 25:1 (1955) at pp. 433–46. In general, the present methods of determining total cholesterol in fluids, particularly in serum, involve the four basic steps of extracting the free cholesterol and the cholesterol esters from the fluid, saponifying the cholesterol esters to free cholesterol, isolating the free cholesterol which results, and determining the isolated free cholesterol. The generally accepted or standard method for determining total cholesterol is the method of Abell, et al. in the Journal of Biological Chemistry, Vol. 195 (1952) at p. 357. In this method the cholesterol esters are saponified by incubation with alcoholic potassium hydroxide, and the free cholesterol is then extracted with petroleum ether. The isolated free cholesterol is determined spectrophotometrically using a modified Liebermann-Burchard reagent (acetic anhydride, sulfuric acid and acetic acid). This standard method and the numerous other available methods possess the clinically disadvantageous characteristic of being highly complicated procedures which use numerous reagents and which are extremely time consuming.

SUMMARY OF THE INVENTION

It has now been found that test compositions and methods for determining both free and total cholesterol may be provided based on the catalyzed degradation reactions of free cholesterol and cholesterol esters. The present invention discloses a test composition for determining free cholesterol in a fluid comprising a chemical system having cholesterol oxidase activity and means for determining hydrogen peroxide. A particularly preferred means for determining hydrogen peroxide comprises a reagent system which includes a substance having peroxidative activity and an indicator material which is oxidized in the presence of peroxide and the substance having peroxidative activity and which changes color thereupon. It is also preferred to include a buffering material which is capable of maintaining a pH of between about 4 and 9 when contacted with the fluid sample. A surfactant capable of solubilizing substantially all of the free cholesterol present in the fluid sample is also preferably included in the test composition for free cholesterol.

A test composition for determining total cholesterol in a fluid is also disclosed comprising a chemical system having cholesterol ester hydrolase activity and the test composition for determining free cholesterol described above. A preferred chemical system having cholesterol ester hydrolase activity comprises the enzyme cholesterol ester hydrolase and a biliary enzyme co-factor therefor. Where the test composition is modified to determine total cholesterol, the buffering material which is preferably included is capable of maintaining a pH of between about 5 and 8 when contacted with the fluid sample. Also, the test composition may include a bacterial inhibitor, such as sodium azide, to prevent interferring bacterial growth.

The disclosed method for determining free cholesterol in a fluid sample comprises contacting the fluid sample with a test composition described above for determining free cholesterol and observing the response which results. It is preferred that the response which results be allowed to develop for a predetermined period of time before observing such response. Also, it is preferred to contact the mixture of the fluid sample and the test composition with an acidic substance in order to enhance the development of the indicator response. Semi-quantitative results are obtained by observing the resulting colorimetric response visually and comparing such response to a standard color chart. Quantitative results are obtained by observing the resulting colorimetric response with instrumental means. Similar method steps are followed for the determination of total cholesterol in a fluid sample; however, the test composition used for this purpose is that which has been previously described for use in determining total cholesterol.

A method for preparing an extract containing cholesterol ester hydrolase which is substantially free of proteolytic activity is also disclosed and includes the steps of combining a substance containing cholesterol ester hydrolase, such as pancreatin, and a first aqueous liquid which may comprise an inorganic salt in solution, separating the liquid and solid phases which are formed thereby, passing the separated liquid phase through a column containing an adsorbent which comprises an adsorbent-active diethylaminoethyl portion, and passing a second aqueous liquid comprising an inorganic salt solution through the column, which inorganic salt solution is capable of eluting cholesterol ester hydrolase from the column. The column adsorbent preferably includes diethylaminoethyl cellulose. A substance capable of protecting cholesterol ester hydrolase from proteolytic activity is also preferably included in both the first and second liquids.

BRIEF DESCRIPTION OF THE DRAWINGS

The sole FIGURE of the drawings is a graphical representation showing the composition of the fractional components of the column effluent using the cholesterol ester hydrolase purification process described in Example 4.

DESCRIPTION OF THE PREFERRED EMBODIMENTS

In the context of this disclosure, determination means either qualitative, semi-quantitative, or quantitative analysis unless otherwise specified.

The present invention is based, in part, on the finding that hydrogen peroxide is formed in the reaction of free cholesterol in the presence of molecular oxygen and certain chemical systems having cholesterol oxidase activity. As used herein, cholesterol oxidase activity refers to the catalysis of free cholesterol through an oxidation reaction which forms hydrogen peroxide as a product. The reaction between such chemical systems and free cholesterol and the subsequent preferred means for determining the hydrogen peroxide which is formed using reagent means can be represented by the following chemical equations:

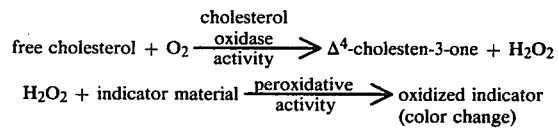

It is contemplated that free cholesterol can also be determined by determining the $\Delta^4$-cholesten-3-one released as well.

It has also been found that when the above system is used in conjunction with a chemical system having cholesterol ester hydrolase activity which is effective to convert the cholesterol esters to free cholesterol, a means for determining total cholesterol is provided. As used herein, cholesterol ester hydrolase activity refers to the catalysis of cholesterol esters to free cholesterol through hydrolysis. This catalysis can be represented by the following equation:

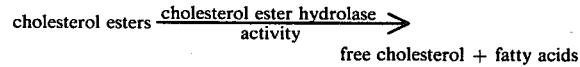

A chemical system having cholesterol oxidase activity can be obtained by a variety of means and in numerous forms. Usually such a system is obtained through the extraction of naturally occurring materials such as microorganisms which may be exemplified by the following: Various Mycobacteria such as *Mycobacterium rubrum*, various Nocardia such as *Nocardia erythropolis*, and various Streptomyces.

A particular chemical system having cholesterol oxidase activity is the enzyme cholesterol oxidase obtained through an extraction of *Mycobacterium rubrum* according to the method disclosed in *Methods in Enzymology* Vol. 1, ed. Colowick and Kaplan, Academic Press (New York, 1955) at pp. 678–81. The preparation may be briefly described as follows. Wet packed cells of *Mycobacterium rubrum* are ruptured by a conventional method such as by grinding in sand. The ground material is suspended in a buffer such as a phosphate buffer and centrifuged to remove the insoluble material. The buffer which contains the soluble protein, of which cholesterol oxidase is a part, is then treated to remove interferring low molecular weight materials such as by dialysis.

A chemical system having cholesterol ester hydrolase activity can be obtained by a variety of means and in numerous forms. Usually such a system is obtained through the extraction of naturally occurring substances such as animal or human pancreas, liver, and intestines. Commercial pancreatin is particularly useful; however, due to its high proteolytic activity content it must undergo purification to remove such activity as will be discussed more fully hereinafter.

According to the present invention, the determination of free cholesterol using a chemical system having cholesterol oxidase activity is dependent upon a means for determining hydrogen peroxide formed by the catalyzed reaction. Such means which can be used include all known techniques for determining hydrogen peroxide in fluids. A particularly preferred means involves the use of a reagent means comprising a substance having peroxidative activity and an indicator material which is oxidized in the presence of peroxide and the substance having peroxidative activity, and which yields a colorimetric response or color change.

Substances having peroxidative activity comprise such naturally occurring peroxidases as horseradish peroxidase and potato peroxidase. Other substances having peroxidative activity include certain organic materials such as normal whole blood, red blood cells alone, lyophilyzed whole blood, urohemin, metalloporphyrins and so forth. Certain inorganic compounds are also useful such as iodide salts and molybdate salts, iron sulfocyanate, iron tannate, ferrous ferrocyanide and potassium chromic sulfate.

Indicator materials of the type disclosed herein include those which are oxidation-reduction indicators having an oxidation-reduction potential appropriate to detecting hydrogen peroxide in the presence of the substance having peroxidative activity. Such indicators include o-tolidine, syringaldazine, vanillinazine, the combination of phenol and 4-aminoantipyrine, 2,7-diaminofluorene, benzidine and derivatives of benzidine such as o-dianisidine.

In the determination of free cholesterol, a buffering material is preferably included in the composition and is preferably capable of maintaining a pH of between about 4 and 9 upon contacting the fluid sample to be tested. Such a pH range assures the stability of the components of the test composition especially where the enzyme cholesterol oxidase is used. The optimum pH range for the detection of free cholesterol using cholesterol oxidase is from about 7.0 to about 7.2. Where a chemical system having cholesterol ester hydrolase activity is included in order to determine total cholesterol, the pH range is preferably between about 5 and 8 with an optimum at 6.6 where the enzyme cholesterol ester hydrolase is used. Any buffering material may be utilized so long as the appropriate pH range criteria are met and the effectiveness of the test composition in detecting free cholesterol or total cholesterol is not substantially impaired.

A surfactant capable of solubilizing substantially all of the free cholesterol present in the fluid sample is preferably included in the test composition for free cholesterol since free cholesterol is only slightly soluble in certain fluids such as aqueous solutions. Where cholesterol ester hydrolase and a biliary co-factor therefor is included to determine total cholesterol, a surfactant is not desirable since the biliary co-factor itself acts as a solubilizing agent. Thus, the use of cholesterol ester hydrolase and its biliary co-factor eliminates all need for a solubilizing agent for free cholesterol, thereby simplifying the test composition. Surfactants which may be used include both ionic and non-ionic surfactants and various other detergents which are well known as solubilizing agents. Bile salts are particularly useful. Those surfactants which function both as solubilizing agents for free cholesterol and as co-factors for cholesterol ester hydrolase include cholic, glycocholic, taurocholic, and taurodeoxycholic acids and their salts. The sodium salts of these compounds are particularly useful.

The disclosed method for detecting free cholesterol or total cholesterol basically comprises contacting the fluid sample to be tested with the appropriate test composition described herein and observing the response which results. The response is preferably a colorimetric response or a color change which is obtained through the use of indicator materials described hereinbefore. The appropriate test composition may be contacted with the fluid sample in a variety of ways, including mixing the fluid sample with a solution, such as an aqueous solution, which contains the test composition. Also, the test composition may be in a dried state, such as a lyophilized state, and added directly to the fluid sample or rehydrated prior to mixing. It is contemplated that the test composition may be incorporated with a carrier member, such as by impregnation of adsorbent pads, to form a test device. Such a device could be dipped into the fluid sample in order to bring the test composition into contact with the fluid sample.

It is preferred to allow the reaction between the components of the test composition and the fluid sample to proceed for a sufficient period of time to promote the development of a sufficient colorimetric response for reliable and sensitive results. This incubation may vary from as short a time as about one minute to a longer period such as overnight. Using the preferred means of detecting hydrogen peroxide, the incubation is usually between about 0.5 hour and 1.0 hour at between about 0° C. and 50° C. and preferably at about 37° C. Also, the addition of an acidic substance such as sulfuric acid to the test composition and fluid sample mixture has been found to enhance the color development using the preferred test composition.

Semi-quantitative results are provided where the response is observed visually and compared to a standard color chart which illustrates the responses developed using known concentrations of free or total cholesterol. Quantitative results are provided using spectrophotometric or reflectance means for determining the response which is then compared to a standard curve.

In the present invention the phrase "chemical system having 'certain' enzymatic activity" implies all chemical compounds singularly or in combination which accomplish the stated enzymatic activity. It is not known whether discrete molecules or enzymes are involved in the activity desired, since the composition is prepared from extracts of naturally occurring substances, which extracts exhibit the desired activity. For example, cholesterol oxidase activity may be provided from an extract of the microorganism *Mycobacterium rubrum* and it is not known whether a single molecule or enzyme is involved. The activity may involve certain enzyme co-factors or more complicated enzyme systems. It is not necessary that enzymes be involved, since the system having cholesterol oxidase activity provides only catalytic activity and does not provide a reagent which is either used up in the reaction or acted upon to produce a product. Thus, the significance is only in resultant catalytic activity and the present invention is therefore described in terms of a chemical system having cholesterol oxidase activity. The same situation applies to cholesterol ester hydrolase activity; however, more is known concerning certain chemical systems having this activity. For instance, it is known that the enzyme cholesterol ester hydrolase requires an enzyme co-factor derived from bile. Those biliary enzyme co-factors include cholic, glycocholic, taurocholic, and taurodeoxycholic acids and their salts.

It is necessary that where the test composition includes proteins such as enzymes in the catalytic chemical system, the test composition be substantially free of proteolytic activity; that is, free of substances capable of promoting the degradation of proteins. If proteolytic activity is present the proteins are destroyed, thereby impairing their participation in the catalytic activity. The enzyme co-factor for cholesterol ester hydrolase inherently protects this enzyme from proteolytic destruction in addition to its function in the catalytic activity of the chemical system. Cholesterol oxidase and peroxidase are not so protected. Thus, where the test composition includes these substances, proteolytic activity must be absent. In the present invention the combination of extracted cholesterol ester hydrolase with such proteins as cholesterol oxidase and peroxidase requires a new method of preparing an extract containing cholesterol ester hydrolase which is substantially free of proteolytic activity.

Such a method is provided comprising the steps of combining a substance containing cholesterol ester hydrolase activity and a first aqueous liquid which may comprise an inorganic salt in solution, separating the resultant liquid and solid phases, passing the liquid phase through a column containing an adsorbent which has an adsorbent-active diethylaminoethyl portion, and passing a second aqueous liquid comprising an inorganic salt solution through the column, which inorganic salt solution is capable of eluting cholesterol ester hydrolase from the column. It has been found that, at an appropriate inorganic salt concentration, cholesterol ester hydrolase has a greater affinity for adsorbents having diethylaminoethyl portions than do those substances having proteolytic activity. A preferred adsorbent is diethylaminoethyl cellulose, although the diethylaminoethyl portion may be attached to a skeletal or supportive portion other than cellulose. Other supportive portions may include the various derivatives of cellulose and so forth.

The first aqueous liquid may or may not include an inorganic salt in solution. Both the first and second aqueous liquids preferably include a buffer in order to maintain a pH environment for cholesterol ester hydrolase which is not deleterious to its catalytic activity. The pH of the buffer is preferably between about 5 and 8 with an optimum at a pH of 6.6. It is further preferred that the inorganic salt itself perform such a buffering function. Particularly useful first and second liquids are potassium phosphate solutions having a concentration of up to 0.05 M and between 0.15 M and 1.0 M respectively. Inorganic salt solutions having ionic strengths equivalent to potassium phosphate solutions within the ranges recited above may also comprise the first and second aqueous liquids. Examples of inorganic salt buffers which may be used include acetate, citrate, tartrate, and phthalate buffers. A particularly useful procedure is described in Example 4 which follows. It is also preferred that both the first and second liquids also comprise a substance capable of protecting cholesterol ester hydrolase from proteolytic activity, such as cholic, glycocholic, taurocholic, and taurodeoxycholic acids and their salts. A bacterial inhibitor may also be included in the first and second aqueous liquids to prevent interferring bacterial growth. A particularly useful bacterial inhibitor is sodium azide.

Fluid samples which can be assayed using the present invention preferably are aqueous solutions where the preferred reagent means for detecting hydrogen peroxide is used. Such fluid samples include body fluids such as serum, urine, plasma, and so forth, as well as other solutions containing free or total cholesterol such as those prepared in laboratory or manufacturing processes.

The test composition may be in the form of a solution such as an aqueous solution, a dried or lyophilized powder, or may be incorporated with a carrier member in a dried state. The components may also be stored separately and combined at the time of use. Suitable carrier members are capable of absorbing the fluid sample being tested and include bibulous paper, cotton, polymeric pads, porous plastics, and so forth. The dry test composition may be impregnated in the carrier member, coated on the carrier member, chemically bonded to the carrier member, physically entrapped within the carrier member or any combination thereof, and so forth. The carrier member may also be attached or otherwise associated with a holder or support.

The present invention provides a means of determining both free and total cholesterol which is simple and rapid with respect to the prior art means. It is eminently suitable for clinical use by personnel having a minimum amount of technical skill and provides an inducement to increase the number of cholesterol determinations requested by physicians. It is particularly surprising to find a workable assay system as highly complex as is presented by the preferred means for detecting total cholesterol. In its preferred embodiment this means comprises the enzymes cholesterol oxidase, cholesterol ester hydrolase, and peroxidase, an enzyme co-factor, and an oxidation-reduction indicator material, yet does not require elaborate control of assay conditions in order to give quantitative results.

The present invention will now be illustrated by the following examples, but is not intended to be limited thereby.

EXAMPLE 1

The formation of hydrogen peroxide from the contacting of a fluid sample containing free cholesterol with a test composition of the present invention is described herein.

A cell-free extract of cholesterol oxidase from *Mycobacterium rubrum* was obtained using the procedure described by Stadtman in *Methods in Enzymology* Vol. I, ed. Colowick and Kaplan, Academic Press (New York, 1955) at pp. 678-81. Three solutions were prepared having the following ingredients:

|  | Enzyme Cholesterol solution ml. | Control solution ml. | Boiled Enzyme Blank solution ml. |
|---|---|---|---|
| 1M Potassium Phosphate buffer (pH 7.5) | 0.2 | 0.2 | 0.2 |
| cholesterol oxidase extract (0.13 units/ml) | 0.8 | 0.8 | — |
| cholesterol oxidase extract boiled for 15 min. | — | — | 0.8 |
| acetone | — | 0.1 | — |
| 1% cholesterol in acetone | 0.1 | — | 0.1 |
| peroxidase/o-dianisidine | 1.0 | 1.0 | 1.0 |

A unit of cholesterol oxidase enzyme activity is defined herein as the amount capable of catalyzing the oxidation of one micromole cholesterol to one micromole $\Delta^4$-cholesten-3-one and one micromole hydrogen peroxide per hour. A unit of cholesterol ester hydrolase enzyme activity is defined herein as the amount capable of catalyzing the hydrolysis of one micromole of cholesteryl oleate per hour. The peroxidase/o-dianisidine solutions contained 1 mg peroxidase/ml and was saturated with respect to o-dianisidine.2HCl. These solutions were incubated at 37° C. for one hour after being purged with molecular oxygen. After incubation, 1 ml of 65% $H_2SO_4$ was added to each solution. The solutions were filtered and the absorbance at 540 nm determined. The control solution and the boiled enzyme blank gave optical densities of 0.080 and 0.020 respectively. The enzyme-cholesterol solution gave an optical density of 0.540 confirming the production of hydrogen peroxide as detected through the oxidation of o-dianisidine.

EXAMPLE 2

This example illustrates the use of the test composition and method of the present invention for the determination of both free and total cholesterol.

The following reagents were prepared:

Cholesterol ester hydrolase—32 units/ml, 9.4 mg protein/ml in 0.1 M potassium phosphate buffer (ph 6.6), 0.28% sodium taurocholate and 0.01% $NaN_3$ Cholesterol oxidase—4 units/ml, 16 mg protein/ml in 0.1 M potassium phosphate buffer (pH 7.0) and 0.01% $NaN_3$ Peroxidase solution—0.1 mg/ml, in 0.1 M potassium phosphate buffer (pH 7.0) and 0.01% $NaN_3$ o-dianisidine—1 mg/ml in 90% ethylene glycol monomethyl ether Buffer—0.1 M potassium phosphate buffer (pH 6.6), 0.28% sodium taurocholate and 0.01% $NaN_3$ Serum—Serachol* standardized serum lot #1560031

These reagents were mixed as follows:

|  | Total Cholesterol Blank ml. | Total Cholesterol Sample ml. | Free Cholesterol Blank ml. | Free Cholesterol Sample ml. |
|---|---|---|---|---|
| Cholesterol ester hydrolase cholesterol | 1.0 | 1.0 | — | — |

| | Total Choles- terol Blank ml. | Total Choles- terol Sample ml. | Free Choles- terol Blank ml. | Free Choles- terol Sample ml. |
|---|---|---|---|---|
| oxidase | 1.0 | 1.0 | 1.0 | 1.0 |
| peroxidase | 0.8 | 0.8 | 0.8 | 0.8 |
| o-dianisidine | 0.2 | 0.2 | 0.2 | 0.2 |
| buffer | — | — | 1.0 | 1.0 |
| serum | — | 0.05 | — | 0.05 |

*The serum used was a standardized serum containing 346 mg/100 ml total cholesterol and 74 mg/100 ml free cholesterol prepared by Warner-Chilcott Laboratories, Morris Plains, New Jersey under the tradename Serachol. The four solutions were then incubated at 37° C. for 1 hour and at the end of that hour the optical densities (OD) at 450 nm were found to be as follows:

| | $OD_{450}$ |
|---|---|
| total cholesterol blank | 0.245 |
| total cholesterol sample | 0.845 |
| free cholesterol blank | 0.140 |
| free cholesterol sample | 0.280 |

Analysis of the data shows that upon subtracting the blanks from both the free and total cholesterol a ratio of 0.233 is obtained between free cholesterol and total cholesterol. This closely matches the known ratio of 0.214 in the standardized serum.

EXAMPLE 3

This example illustrates that increasing levels of free cholesterol yield increasing colorimetric responses using the preferred detection means for free cholesterol.

0.5 mg/ml and 1.0 mg/ml free cholesterol standard acetone solutions were prepared. 0.5 ml of an enzyme solution containing cholesterol oxidase 0.13 units/ml and 0.5 ml of a peroxidase/o-dianisidine solution containing 1 mg peroxidase/ml and saturated with o-dianisidine.2HCl. were each added to 0.05 ml of the standard solutions and 0.05 ml of a control solution comprising 0.05 ml acetone. The three solutions were purged with molecular oxygen and incubated at 37° C. for 1.0 hour at which time 1 ml of 65% $H_2SO_4$ was added. Optical density (OD) was measured at 540 nm to give the following results:

| | $OD_{540}$ |
|---|---|
| control | 0.07 |
| 0.5 mg/100 ml | 0.12 |
| 1.0 mg/100 ml | 0.21 |

EXAMPLE 4

This example relates to the preparation of extracted cholesterol ester hydrolase which is substantially free of proteolytic activity.

A solution of 10 g. commercial pancreatin 4XNF (prepared by the method of *National Formulary XIII* American Pharmaceutical Association, Washington, D.C., 1970) in 100 ml of 0.05 M potassium phosphate buffer (ph 6.6), 0.28% sodium taurocholate, and 0.01% $NaN_3$ was stirred at room temperature for about 30 minutes. 1 ml of this pancreatin suspension was mixed with 2 ml of 0.05 M potassium phosphate buffer (pH 6.6) 0.28% sodium taurocholate, and 0.01% $NaN_3$ and assayed for enzymatic activity using the procedure of Example 5. The remaining volume of suspension was divided into four equal volumes and centrifuged for 30 minutes at 15,000 rpm and 4° C. The supernatants were combined and 0.1 ml of this buffer extract was mixed with 9.9 ml of 0.1 M potassium phosphate buffer (pH 6.6), 0.28% sodium taurocholate, and 0.01% $NaN_3$. This diluted extract was assayed for protein using the method described in *Methods in Enzymology* Vol. III, ed. Colowick and Kaplan, Academic Press (New York, 1957) at pp. 451–4. Also, 0.1 ml of the buffer extract was mixed with 0.2 ml of 0.1 M potassium phosphate buffer (pH 6.6), 0.28% sodium taurocholate, and 0.01% $NaN_3$ and assayed for enzymatic activity using the procedure of Example 5.

DE-52 (DEAE-cellulose) manufactured by Whatman Biochemicals Ltd., Maidstone, Kent, England, was washed in 0.05 M potassium phosphate buffer (pH 6.6), 0.28% sodium taurocholate, and 0.01% $NaN_3$ and added as a slurry to a 5 cm.×90 cm. column to form a 1 liter bed volume with a 200 ml volume of the washing buffer remaining on top of the bed. The entire 4 liter volume of the phosphate buffer extract was then added to the column, followed by 50 ml of a first eluting buffer of 0.05 M potassium phosphate buffer (pH 6.6), 0.28% sodium taurocholate, 0.01% $NaN_3$, and 0.01 M mercaptoethanol. A second eluting buffer was then continuously added consisting of 0.2 M potassium phosphate buffer (pH 6.6), 0.28% sodium taurocholate, 0.01% $NaN_3$, and 0.01 M mercaptoethanol. The column effluent was collected in 22 ml fractions which were assayed for enzymatic activity using the procedure that follows this Example and for protein as above. The results are found in the following table and in the graph illustrated in the FIGURE of the drawing.

| | Vol. ml. | Protein mg. | Enzyme Activity Units | Specific Activity Units/ mg. | Recovery % |
|---|---|---|---|---|---|
| pancreatin suspension | 105 | 10,000 | 3150 | 0.3 | 100 |
| buffer extract | 91 | 5,960 | 1840 | 0.3 | 58 |
| DEAF-cellulose | 103 | 260 | 850 | 3.3 | 27 |

The cholesterol ester hydrolase containing effluent fractions were combined and the volume concentrated to about 100 ml on a Diaflo UM-10 ultrafiltration membrane manufactured by Amicon Corporation, Lexington, Massachusetts and then dialyzed against 100 volumes of 0.05 M potassium phosphate buffer (pH 6.6), 0.28% sodium taurocholate, and 0.01% $NaN_3$ at 4° C. overnight with one buffer change.

The 0.2 M potassium phosphate buffer (pH 6.6), 0.28% sodium taurocholate, 0.01% $NaN_3$ and 0.01 M mercaptoethanol effluent fractions were found to contain no proteolytic activity from either trypsin or chymotrypsin.

EXAMPLE 5

The following relates to the preparation of the cholesteryl oleate substrate for use in determining cholesterol ester hydrolase activity and to the assay procedure itself.

a. Substrate preparation

Ten mg cholesteryl oleate and 18 mg DL-lecithin were dissolved in 1 ml of ethyl ether in a homogenizing tube fitted with a teflon plunger. Six ml of 0.1 M potassium phosphate buffer (pH 6.6), 0.28% sodium taurocholate, and 0.01% $NaN_3$ were then added and the mixture was homogenized using the plunger for 5 minutes. The ether was removed by holding the tube under hot running water with occasional activation of the plunger over a 15 minute period. The solution was cooled in an ice bath and subjected to sonication for 15 minutes using a Sonifier ® cell disrupter Model W140 and a Sonifier ® converter Model L, manufactured by Branson Sonic Power Company, Plainview, New York. The solution was then centrifuged at 2500 rpm for 15 minutes and the insoluble material discarded.

b. Assay procedure

Twenty-five $\mu l$ of the enzyme solution was added to one ml of the substrate solution preheated to 37° C. and incubated at 37° C. for 10 minutes. Four ml of Bloor's solvent (75% ethyl alcohol:25% ethyl ether) were added and the solution was centrifuged at 2000 rpm for 10 minutes. One ml of the supernatant was mixed with 1 ml of a 1.0% digitonin solution in 50% ethyl alcohol:50% water. The precipitate was allowed to coagulate for twelve hours and the solution was then centrifuged at 2500 rpm for 15 minutes. The precipitate was washed with 4 ml acetone and centrifuged again. This precipitate was dried in a gentle stream of air at room temperature and 3 ml of 0.1% $FeCl_3.6H_2O$ in glacial acetic acid was added to dissolve the precipitate. Two ml of conc. $H_2SO_4$ was added slowly forming two layers which were quickly mixed and the optical density measured at 560 nm. These values were then divided by the optical density of a sample containing a known amount of free cholesterol subjected to the same assay procedure. In order to obtain results in terms of units/ml as defined herein, the quotients were then multiplied by time and dilution factors to yield results in terms of $\mu$moles cholesterol per ml per hour. Specifically, 0.1 $\mu$mole free cholesterol was subjected to the above assay procedure using 2.5 ml of the supernatant yielding an optical density of 1.248. Since the assay time was 10 minutes and the volume used was 25 $\mu l$, the time and dilution factors were 6 and 40 respectively and cholesterol ester hydrolase activity was calculated as follows:

$$\text{units/ml} = (OD_{560}/12.48) \times 240$$

What is claimed is:

1. A test device for use in determining total cholesterol in a biological fluid sample comprising a test composition which includes a chemical system having cholesterol ester hydrolase activity, a chemical system having cholesterol oxidase activity, and means for determining at least one of the reaction products produced when free cholesterol is contacted with said chemical system having cholesterol oxidase activity; and a carrier for said test composition.

2. A test device as in claim 1 wherein said carrier is absorbent relative to said fluid sample.

3. A test device as in claim 1 wherein said test composition additionally includes a buffering material.

4. A test device as in claim 1 wherein said chemical system having cholesterol ester hydrolase activity comprises cholesterol ester hydrolase and a biliary enzyme co-factor therefor.

5. A test device as in claim 1 wherein said means for determining at least one of the reaction products produced when free cholesterol is contacted with said chemical system having cholesterol oxidase activity comprises means for determining hydrogen peroxide which means comprises a substance having peroxidative activity and an indicator material which is oxidized in the presence of peroxide and said substance having peroxidative activity and which changes color thereupon.

* * * * *